(12) United States Patent
Ng et al.

(10) Patent No.: US 11,779,929 B2
(45) Date of Patent: Oct. 10, 2023

(54) FIBRIN CLOT PREPARATION INSTRUMENTS AND METHOD

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jennifer Ng, Seattle, WA (US); Charles H. Brown, Jr., Wellesley, MA (US); William R. Davis, Hingham, MA (US)

(73) Assignees: SMITH & NEPHEW, INC., Memphis, TN (US); SMITH & NEPHEW ORTHOPAEDICS AG, Zug (CH); SMITH & NEPHEW ASIA PACIFIC PTE. LIMITED, Singapore (SG)

( * ) Notice: Subject to any disclaimer, the term of this patent is extended or adjusted under 35 U.S.C. 154(b) by 163 days.

(21) Appl. No.: 16/995,121

(22) Filed: Aug. 17, 2020

(65) Prior Publication Data
US 2021/0060546 A1 Mar. 4, 2021

Related U.S. Application Data

(60) Provisional application No. 62/894,994, filed on Sep. 3, 2019.

(51) Int. Cl.
*B01L 3/00* (2006.01)
*A61L 27/36* (2006.01)

(52) U.S. Cl.
CPC ........... *B01L 3/508* (2013.01); *A61L 27/3616* (2013.01); *B01L 2400/0457* (2013.01)

(58) Field of Classification Search
CPC .. A61L 24/0042; A61L 24/106; A61L 27/225; A61L 27/3616; A61L 15/32; B01L 3/508; B01L 2400/0457; A61K 38/36; A61M 1/0259; A61J 1/14
See application file for complete search history.

(56) References Cited

U.S. PATENT DOCUMENTS

| | | |
|---|---|---|
| 4,790,819 A | 12/1988 | Li et al. |
| 2010/0228175 A1 | 9/2010 | Pierce et al. |
| 2010/0330659 A1* | 12/2010 | Poulsen ............... G01N 1/2813 435/283.1 |

(Continued)

FOREIGN PATENT DOCUMENTS

| | | |
|---|---|---|
| RU | 2273487 C2 | 4/2006 |
| WO | 2018169719 A1 | 9/2018 |

OTHER PUBLICATIONS

European Search Report Application No. 20190961.1-1115 dated Jan. 28, 2021.

*Primary Examiner* — Matthew D Krcha
*Assistant Examiner* — Austin Q Le
(74) *Attorney, Agent, or Firm* — Burns & Levinson, LLP; Joseph M. Maraia; Marlo Schepper Grolnic (57) ABSTRACT

Embodiments of the invention include instruments and methods useful in preparing and delivering graft material to a surgical site. Some embodiments may particularly be directed to forming a graft from a blood clot and accurately and effectively handling and delivering the graft to a surgical site. Graft material may include blood components such as clotted fibrin derived from a patient's or a donor's blood.

12 Claims, 10 Drawing Sheets

(56) References Cited

U.S. PATENT DOCUMENTS

| | | | |
|---|---|---|---|
| 2011/0021334 A1* | 1/2011 | Leach | G01N 33/491 494/37 |
| 2015/0072362 A1* | 3/2015 | Lui | G01N 1/02 600/572 |
| 2017/0285047 A1 | 10/2017 | Grimberg et al. | |
| 2018/0311404 A1* | 11/2018 | da Silva Junior | A61M 1/0259 |
| 2019/0133881 A1* | 5/2019 | Orava | A61M 1/3693 |

* cited by examiner

FIBRIN CLOT PREPARATION INSTRUMENTS AND METHOD

CROSS-REFERENCE TO RELATED APPLICATIONS

This application claims priority to and benefit of U.S. Provisional Application No. 62/894,994, filed Sep. 3, 2019, entitled FIBRIN CLOT PREPARATION INSTRUMENTS AND METHOD, the entire contents of which are incorporated herein by reference for all purposes.

FIELD OF THE INVENTION

The present invention relates generally to the field of medical devices, and more particularly relates to instruments and methods for preparing and delivering tissue healing substances to a tissue repair surgical site. Some embodiments of the invention are specifically directed to preparing and delivering fibrin clots to a tissue repair surgical site.

BACKGROUND

Tissue healing is often enhanced in the presence of concentrations of bioactive substances in blood. For example, meniscal tear healing can be improved in the presence of blood components, especially in concentrated forms. It is believed that meniscal repairs accomplished in conjunction with anterior cruciate ligament reconstruction are particularly advantageous. Insertion of a fibrin clot in a meniscal tear prior to the tear being sutured or otherwise closed is advantageous.

It is known in the prior art to draw a patient's blood into a syringe and transfer the blood into a metal pan or a beaker. A glass syringe barrel, a metal rod stirrer, or another stirring implement may then be used to stir the blood until coagulation takes place. The time to form a clot depends on materials, sizes, and surface areas of the vessel and stirrer. In some methods, the clot is removed from the stirrer and transferred to a gauze pad. The clot may then be flattened to a consistent thickness and then cut or shaped to make a desired clot graft shape. Such a clot can be inserted into a damaged tissue site. For meniscal repair, such a clot can be transported arthroscopically through a portal, past a patient's fat pad, and into the meniscal tear. This processes is very technically demanding due to the small size and fragile consistency of the clot in combination with difficulties associated with accessing the tissue repair site.

It would be advantageous to provide instruments and methods that enable more consistent and less technically demanding forming, handling, and delivery of clot graft material, such as a fibrin clot. For example, it would be an improvement to provide instruments and methods that enabled formation of a graft that has been better drained of fluids while being prepared, for example, being drained while on the gauze pad. Some improved embodiments may include multi-purpose instruments that may be used for two or more of forming a fibrin clot from collected blood, handling the fibrin clot, removing excess liquid from the fibrin clot, and flattening the fibrin clot. Some improved embodiments may include instruments for delivering the graft to the tissue repair site.

SUMMARY

An embodiment of the invention is a clot preparation device that includes a base, a work surface supported on the base, and a drainage opening through the work surface. Embodiments of the work surface include an upper working area, and a perimeter around the upper working area in at least part of which is formed a channel that is lower than an adjacent part of the upper working area so that fluid placed on the upper working area will drain into the channel under the force of gravity when the base is placed on a horizontal surface.

Another embodiment of the invention is a combination clot forming tool that includes a handle with a first diameter about a longitudinal axis of the combination clot forming tool and a roller coupled to the handle with a second diameter about the longitudinal axis of the combination clot forming tool that is greater than the first diameter of the handle. The clot forming tool may also include a clot collection end coupled to the roller with a third diameter about the longitudinal axis of the combination clot forming tool that is less than the second diameter of the roller, and the clot collection end may include a surface configured to enhance formation of a blood clot when passed through blood.

Yet another embodiment of the invention is an instrument set that includes a clot preparation device with a base, a work surface supported on the base, and a drainage opening through the work surface. The work surface may include an upper working area, and a perimeter around the upper working area in at least part of which is formed a channel that is lower than an adjacent part of the upper working area so that fluid placed on the upper working area will drain into the channel under the force of gravity when the base is placed on a horizontal surface. Instrument set embodiments may also include a combination clot forming tool with a handle with a first diameter about a longitudinal axis of the combination clot forming tool, a roller coupled to the handle with a second diameter about the longitudinal axis of the combination clot forming tool that is greater than the first diameter of the handle, and a clot collection end coupled to the roller with a third diameter about the longitudinal axis of the combination clot forming tool that is less than the second diameter of the roller. The clot collection end may also include a surface configured to enhance formation of a blood clot when passed through blood. Instrument set embodiments may also include a delivery device configured to be held in the clot preparation device.

Still another embodiment of the invention is a method of delivering graft material to a surgical site that includes forming a clot on a portion of a clot forming tool that has a first diameter, and moving the clot from the clot forming tool to a clot preparation device that includes a base and a work surface supported on the base. The work surface may include an upper working area, and a perimeter around the upper working area in at least part of which is formed a channel that is lower than an adjacent part of the upper working area so that fluid placed on the upper working area will drain into the channel under the force of gravity when the base is placed on a horizontal surface. The work surface may also include a drainage opening through the work surface. The method may also include pressing the clot against the upper working area to remove liquid from the clot with a portion of the clot forming tool that has a second diameter larger than the first diameter, and delivering a portion of the pressed clot to the surgical site.

DETAILED DESCRIPTION

This application incorporates by reference in its entirety U.S. Provisional Application No. 62/471,419, "Graft Preparation and Delivery Instruments and Method," which was filed Mar. 15, 2017 and was also published on Sep. 20, 2018 as WO2018/169719A1, Appl. No. PCT/US2018/020999.

Figure 1A:
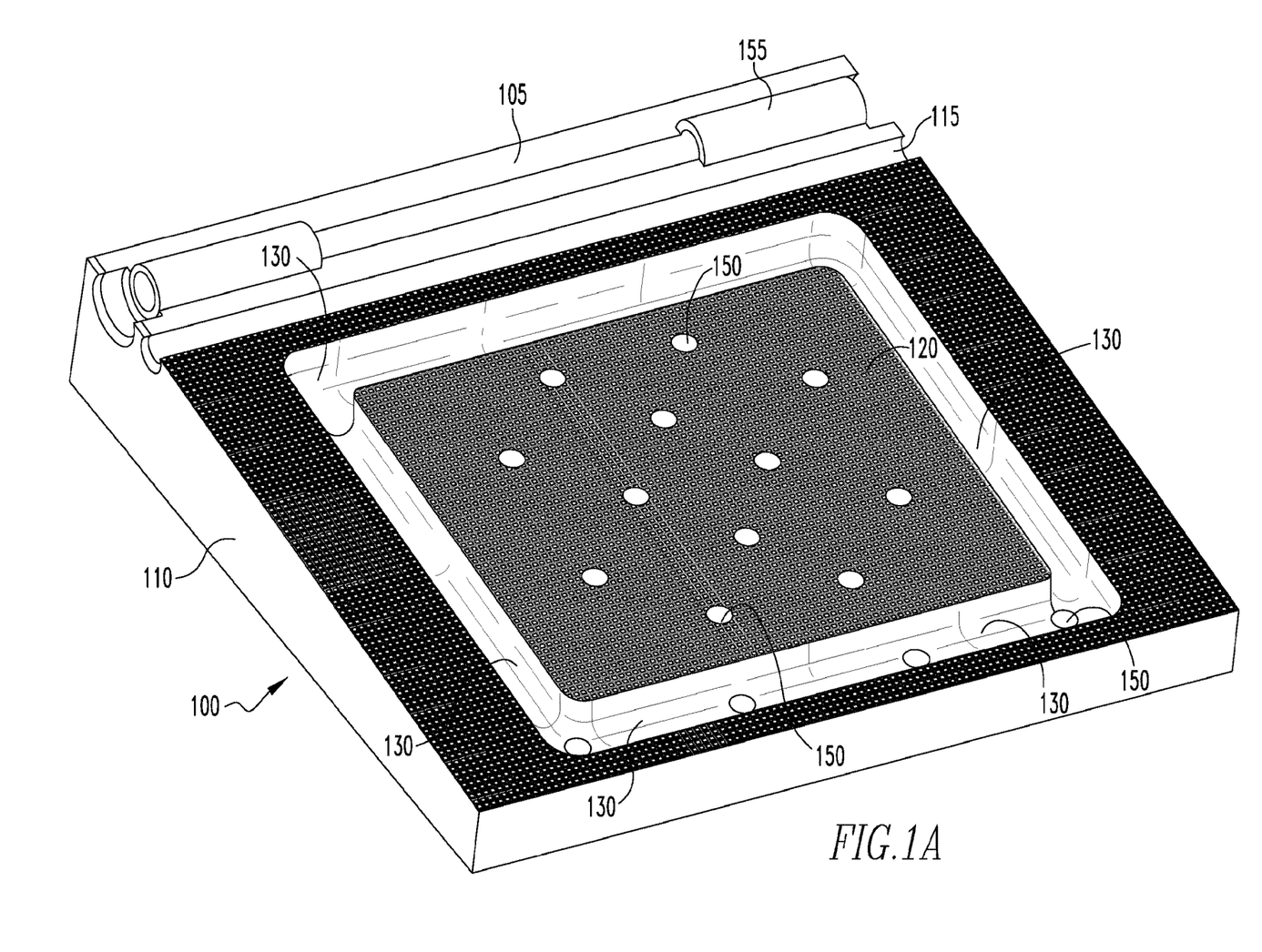
FIG. 1A is a perspective view of an embodiment of a clot preparation device.
Figure 1B:
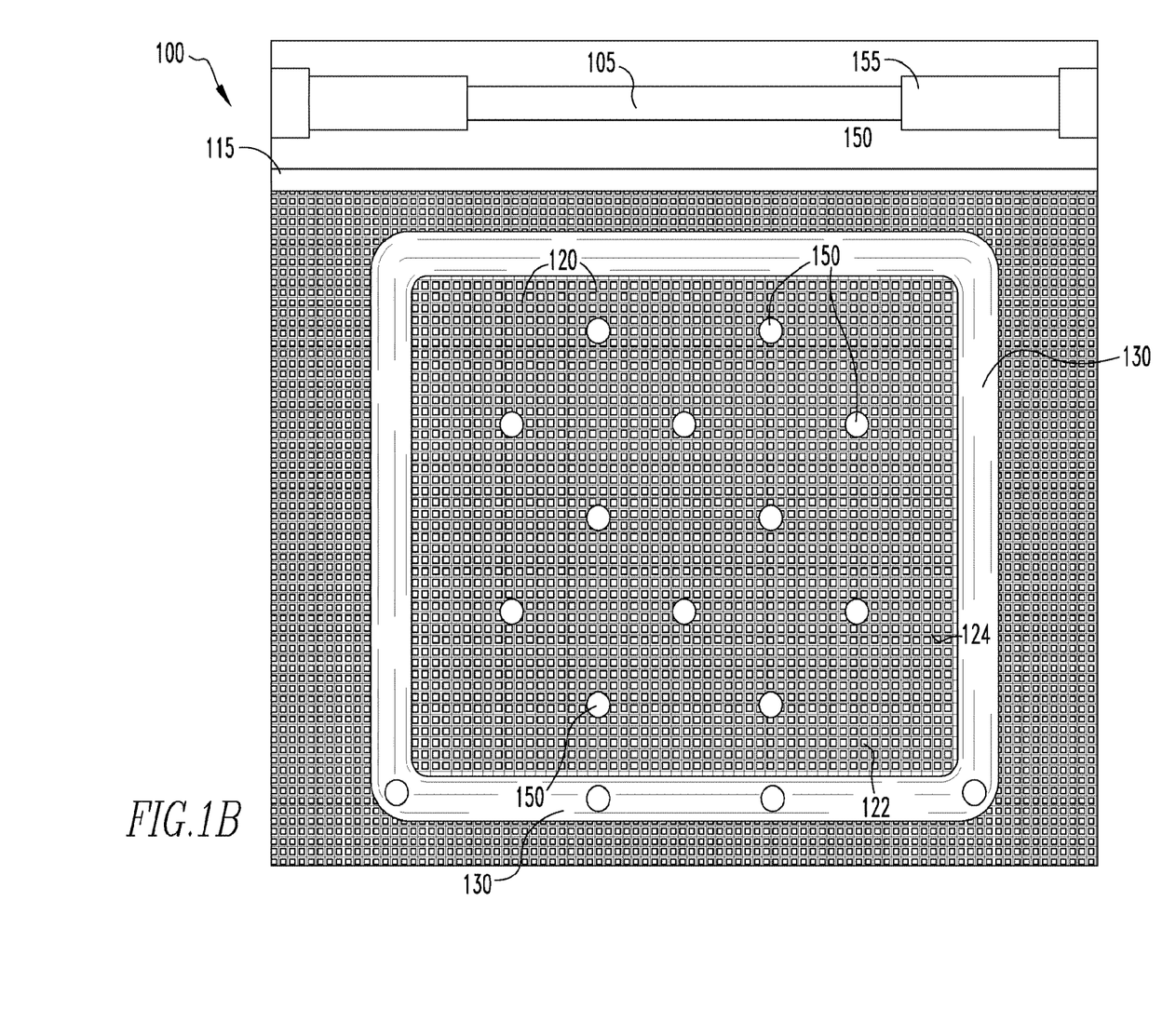
FIG. 1B is a perspective view of a top portion of the clot preparation device of FIG. 1A.

An embodiment of a clot preparation device 100 is illustrated in FIGS. 1A, 1B, 5, 6, 8, and 9. The clot preparation device 100 includes a base 110, a work surface 120 supported on the base 110, and multiple drainage openings 150. As most clearly shown in the FIG. 1A illustration, the base 110 supports the work surface 120, that is sloped from horizontal when the base 110 is placed on a horizontal surface. This enables a sloped work surface 120. The depicted slope is toward the operator, but in other embodiments, the slope may be in another effective direction. The work surface 120 illustrated has an upper working area 122, and a perimeter 130 around the upper working area 122. In the embodiment illustrated, the upper working area 122 includes the peaks of knurls created in the work surface 120 (FIG. 1B).

Figure 8:
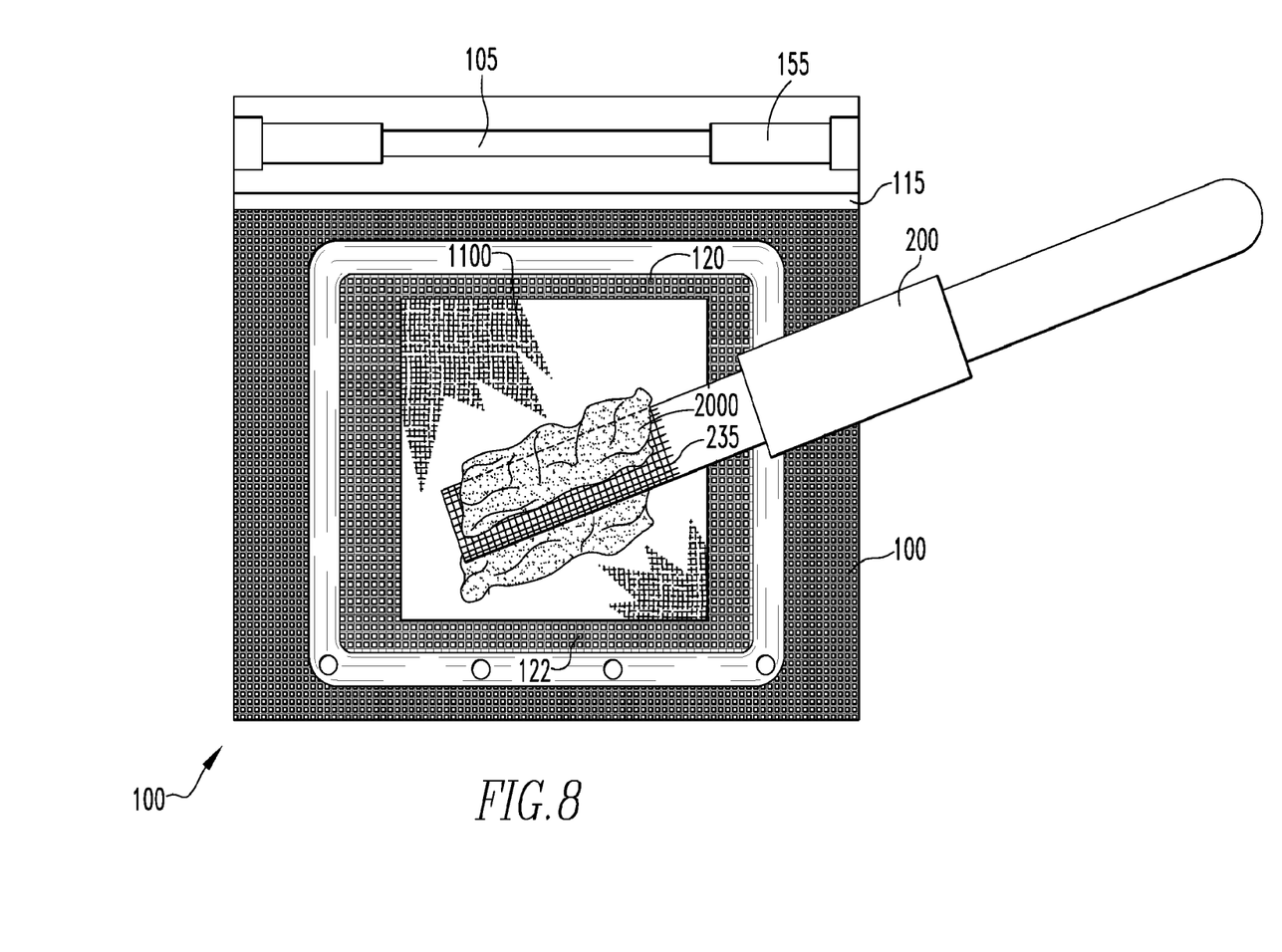
FIG. 8 is a perspective view of a top of the clot preparation device of FIG. 1B with the clot forming tool of FIG. 2 depositing clot material on a gauze pad.
Figure 9:
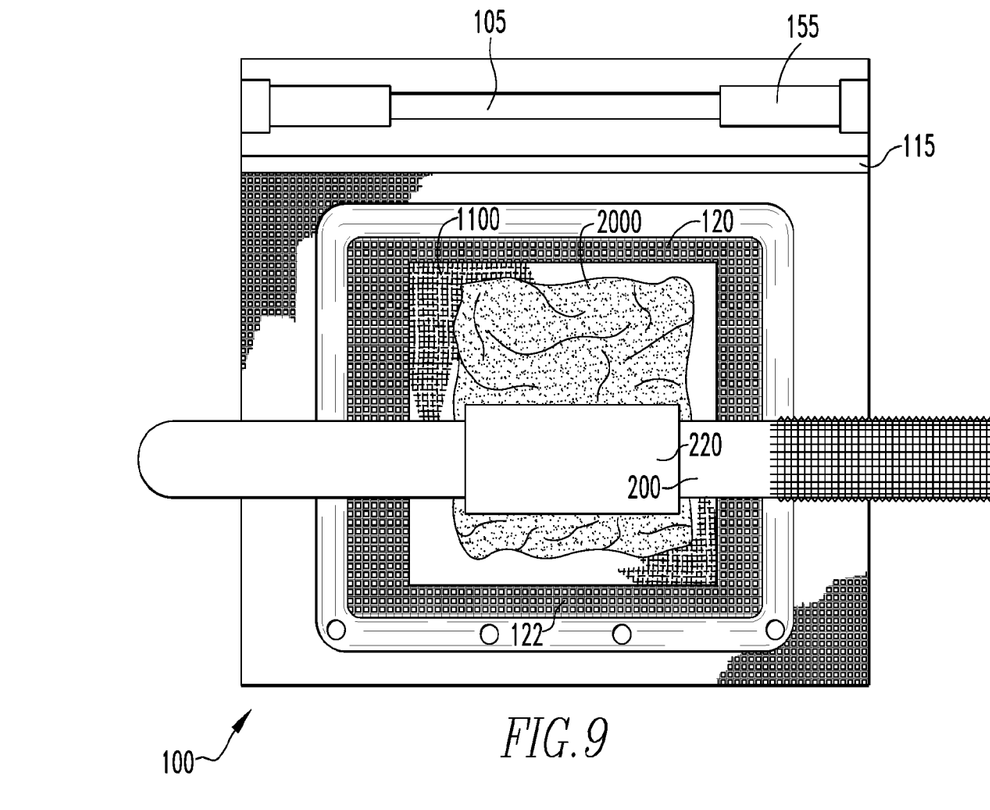
FIG. 9 is a perspective view of a top of the clot preparation device of FIG. 1B with the clot forming tool of FIG. 2 preparing clot material on a gauze pad.

The perimeter 130 depicted includes a channel that is at least in part lower than an adjacent part of the upper working area 122 so that fluid placed on the upper working area 122 will drain into the channel under the force of gravity when the base 110 is placed on a horizontal surface. As used here, "lower" means at a lesser elevation when the clot preparation device 100 is sitting on its base 110 on a horizontal surface. The illustrated channel in the perimeter 130 extends around the entire perimeter 130, but in other embodiments, the channel may be in only a portion of the perimeter 130. The work surface 120 depicted includes a lower working area 124 below the upper working area 122 configured such that fluid placed on the upper working area 122 will drain into the lower working area 124 under the force of gravity when the base 110 is placed on a horizontal surface. In the embodiment illustrated, the lower working area 124 includes the valleys of the knurls (FIG. 1B). As shown, there are two or more sloped regions between the knurl peaks of the upper working area 122 and the knurl valleys of the lower working area 124. As illustrated in FIGS. 8 and 9, the knurl peaks at the upper working area 122 are configured to support a clot 2000 being prepared on the clot preparation device 100. Particularly, in the illustrated embodiment, support of the clot 2000 is also provided by a gauze pad 1100 that rests primarily on the knurl peaks of the upper working area 122. In other embodiments, another material may be substituted for gauze or an additional support component such as the gauze pad 1100 may be omitted. The valleys of the lower working area 124 shown extend in two directions, but in other embodiments may only extend in one direction or may extend in more than two directions. In some embodiments, a clot may be another type of graft material, such as but not limited to, autograft, allograft, a synthetic graft, or any substance or composition which is useful in the healing of tissue. For example and without limitation, clots or grafts of various embodiments of the invention may be blood components, such as fibrin derived from blood, collagen, ligaments, tendons, or any combinations or components of any of these.

Multiple drainage openings 150 are shown in the channel in FIGS. 1A and 1B and through more central portions of the work surface 120. However, in other embodiments, one or more drainage openings 150 may be located only in the channel around the perimeter 130 and not necessarily in more central portions of the work surface 120. In still other embodiments, one or more drainage openings 150 may be located only in more central portions of the work surface 120 and not in the channel around the perimeter 130.

Figure 4:
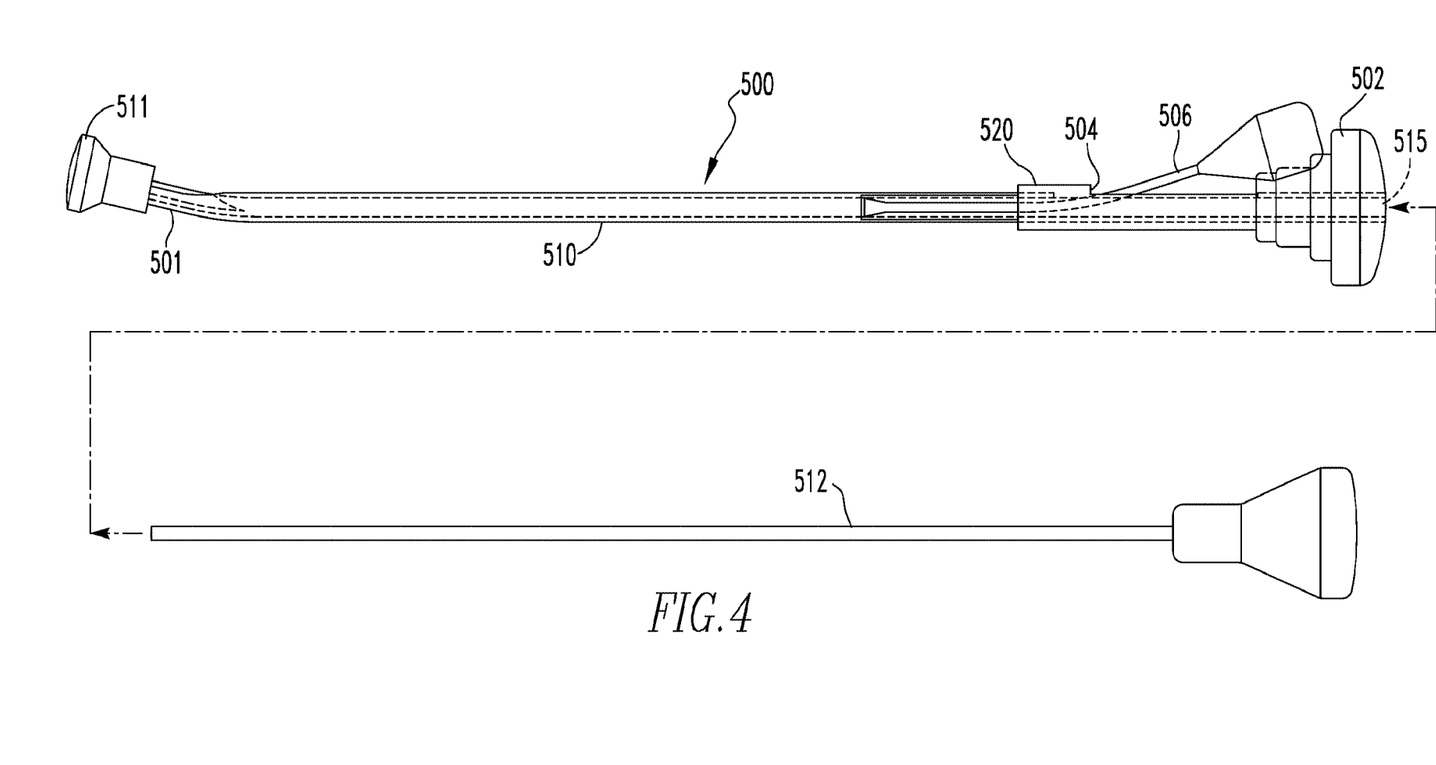
FIG. 4 is a perspective view of a side of an embodiment of a clot delivery device.
Figure 5:
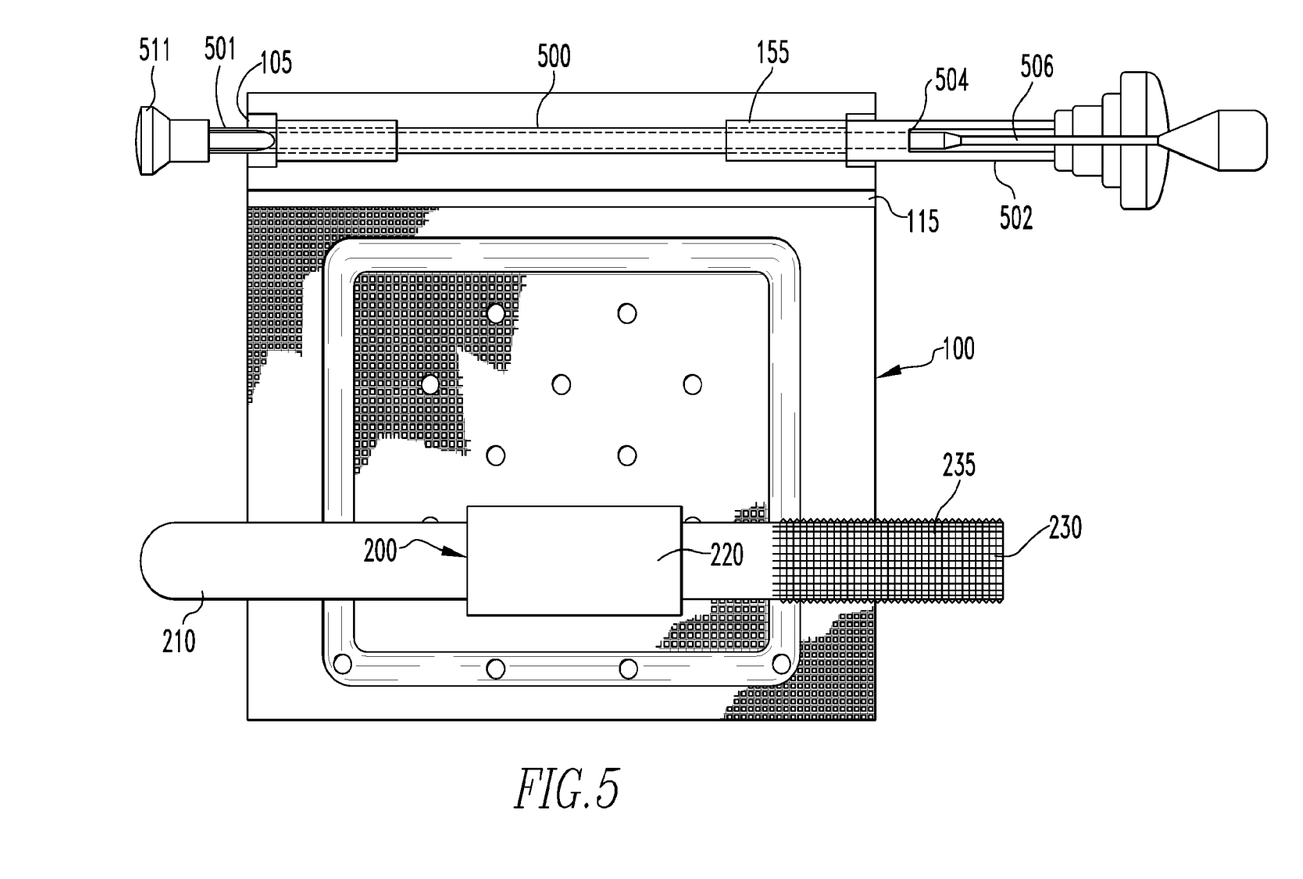
FIG. 5 is a perspective view of a top of the clot preparation device of FIG. 1B with the clot forming tool of FIG. 2 and the clot delivery device of FIG. 4.
Figure 6:
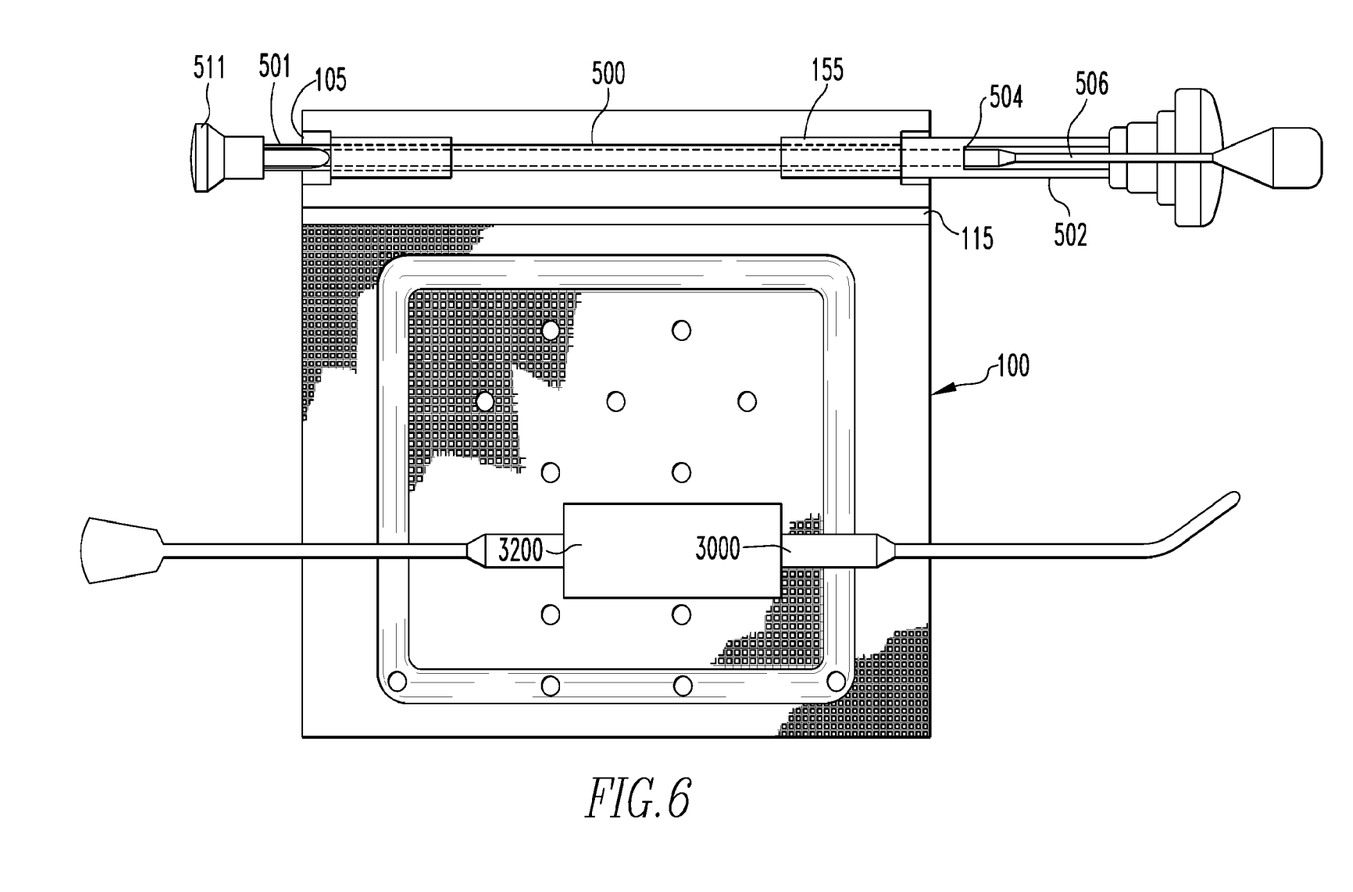
FIG. 6 is a perspective view of a top of the clot preparation device of FIG. 1B with an alternate combination clot forming tool and the clot delivery device of FIG. 4.

As shown in FIGS. 1A, 1B, 5, 6, 8, and 9, the clot preparation device 100 may include a delivery device holder 105 comprising an indention in the clot preparation device 100. Additionally, the clot preparation device 100 may include a supplemental delivery device holder 115 configured to receive an additional delivery device 500. An example of a delivery device 500 is depicted in FIGS. 4-6. The delivery device 500 includes a tubular body 510, a distal end 501, a proximal end 502, a proximal opening 515 through which a proximal plunger 512 may be inserted, and a portal 504 through which graft material and a plunger 506 may be inserted. The proximal plunger 512 and the plunger 506 are configured to move within the delivery device 500 proximally-distally to move graft material through and potentially out of the distal end 501 of the delivery device 500. A sleeve 520 is also illustrated rotatably coupled around the tubular body 510 adjacent to the portal 504. The sleeve 520 includes an opening and may be rotated relative to the tubular body 510 to close or open the portal 504. The delivery device 500 also includes a cap 511 at the distal end 501 that is removable. Several other delivery devices that could be used in various embodiments are disclosed in WO2018/169719A1, which has been incorporated by reference herein in its entirety. The various delivery device embodiments are referred to in that application as an, "instrument for containing a graft configured for delivery."

The delivery device holder 105 or the supplemental delivery device holder 115 may receive the delivery device 500, the delivery devices incorporated by reference, and any other delivery devices that will couple into the holders provided. In the illustrated embodiment, the clot preparation device 100 also includes a delivery device holder connector 155 into which a part of a delivery device, such as the delivery device 500, is releasably connectable. In one example (FIGS. 5 and 6), the delivery device holder connector 155 couples with the tubular body 510 of the delivery device 500 to hold the delivery device 500 relative to the clot preparation device 100.

An embodiment of a combination clot forming tool 200 is illustrated in FIGS. 2, 3, 5, 8, and 9. The combination clot forming tool 200 shown includes a handle 210 with a first diameter about a longitudinal axis of the combination clot forming tool 200 and a roller 220 coupled to the handle 210. The roller 220 illustrated has a second diameter about the longitudinal axis of the combination clot forming tool 200 that is greater than the first diameter of the handle 210. As shown in FIG. 9, the roller 220 may have a smooth surface configured to press against and flatten a blood clot 2000 without substantially adhering to the blood clot 2000 when rolled over the blood clot 2000. The smooth surface of the roller 220, or other embodiments of a roller, may be made from the same material as all or part of the remainder of the clot forming tool 200. For example, the material may be plastic, glass, or metallic. In other embodiments, a roller of a clot forming tool may be a special material or coating engineered to reduce adhesion to a blood clot or other graft material. An alternate embodiment of a roller is a roller attachment 3200 (FIG. 6). The roller attachment 3200 is removably connectable to an instrument for positioning a graft 3000. Embodiments of the instrument for positioning a graft may include at respective ends: elevators, spatulas, paddles with various curvatures or shapes, graspers, hooks, etc., to enable various angles of approach to a graft or for the handling of different types of graft. The "handling instruments" shown in WO2018/169719A1, which is incorporated by reference herein in its entirety, provide illustrations of other possible end configurations for embodiments of the instrument for positioning a graft. Other embodiments of the handling instrument would not necessarily include a paddle or other handling component on each end of the handling instrument.

Figure 7:
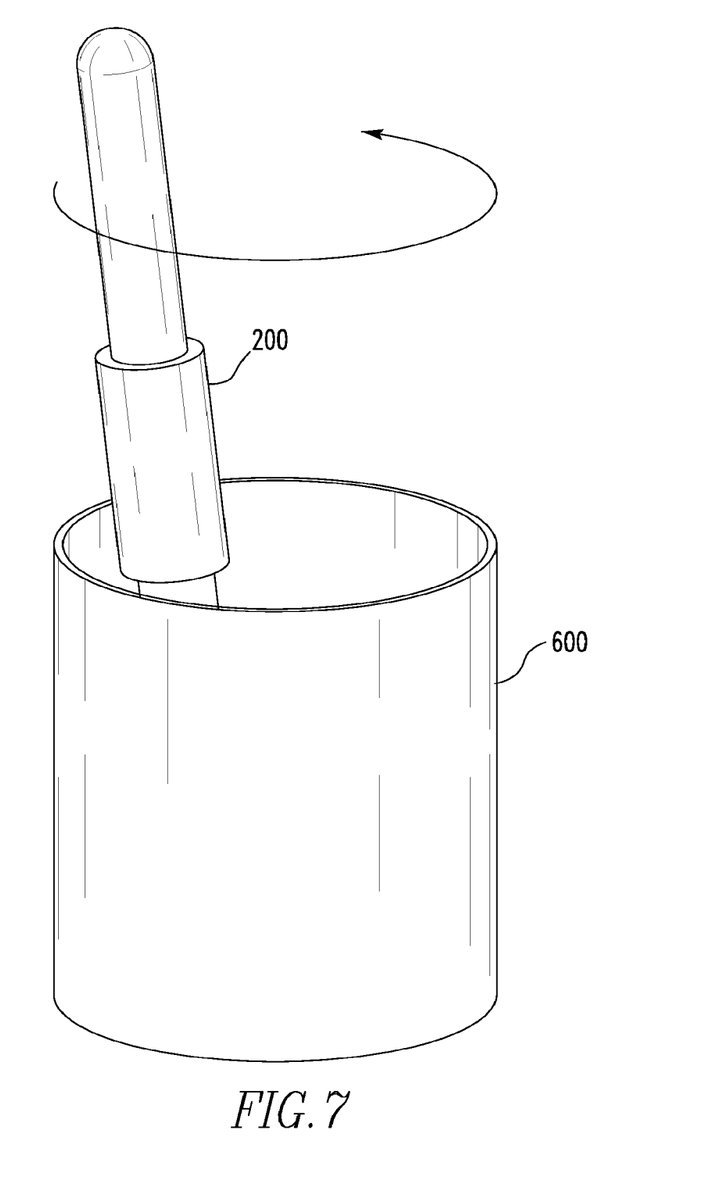
FIG. 7 is a perspective view of a cup in use with the combination clot forming tool illustrated in FIG. 2.

The clot forming tool 200 shown also includes a clot collection end 230 coupled to the roller 220. The clot collection end 230 has a third diameter about the longitudinal axis of the combination clot forming tool 200 that is less than the second diameter of the roller 220. The clot collection end 230 depicted has a surface 235 configured to enhance formation of a blood clot when passed through blood. Such use is shown in FIG. 7 where the clot collection end 230 is being used to agitate blood in a cup 600. The surface 235 is a knurled surface with intersecting peaks and valleys in two substantially perpendicular directions. Other embodiments may include etched surfaces, roughened surfaces, scored surfaces, coated surfaces, or other surface treatments, or portions with surfaces made from other materials upon which clots form, such as, but not limited to: glass, ceramic, and corrosion resistant metals such as stainless steel. As most easily seen in FIG. 3, the clot collection end 230 may include a tubular shape with a cannulation 233. Other embodiments may have different wall thicknesses or be partially or completely solid.

An embodiment of the invention is an instrument set that includes the clot preparation device 100, the combination clot forming tool 200, and one or more of the delivery devices 500 configured to be held in the clot preparation device 100. Instrument set embodiments may include any of the variations of the clot preparation device, combination clot forming tool, and the delivery devices disclosed. Instrument set embodiments may also include two or more delivery devices. In some embodiments, the instrument set may also include an instrument for positioning a graft, such as the instrument for positioning a graft 3000 described in association with FIG. 6. The alternate embodiment of the roller, the attachment roller 3200, is illustrated in use in FIG. 6. The roller attachment 3200 illustrated is configured to be removably coupled to the instrument for positioning a graft 3000. The roller attachment 3200 shown includes a smooth surface configured to press against and flatten a clot, such as the clot 2000, without substantially adhering to the clot 2000 when rolled over the clot 2000. The smooth surface of the roller attachment 3200 may be made from the same material as all or part of the remainder of the instrument for positioning a graft 3000. For example, the material may be metallic, plastic, or glass. In other embodiments, a roller of a clot forming tool may be a special material or coating engineered to reduce adhesion to a blood clot or other graft material.

The instrument set may also include the cup 600, as illustrated in FIG. 7. The cup 600 may be made from any type of material able to be sterilized effectively that will not unnecessarily adhere to the graft or clot material being prepared. For example and without limitation, the cup 600 may be made from glass or stainless steel. Embodiments of the cup 600 are not limited to a cylindrical container open at one end and may be any shape or size of effective container.

Figure 2:
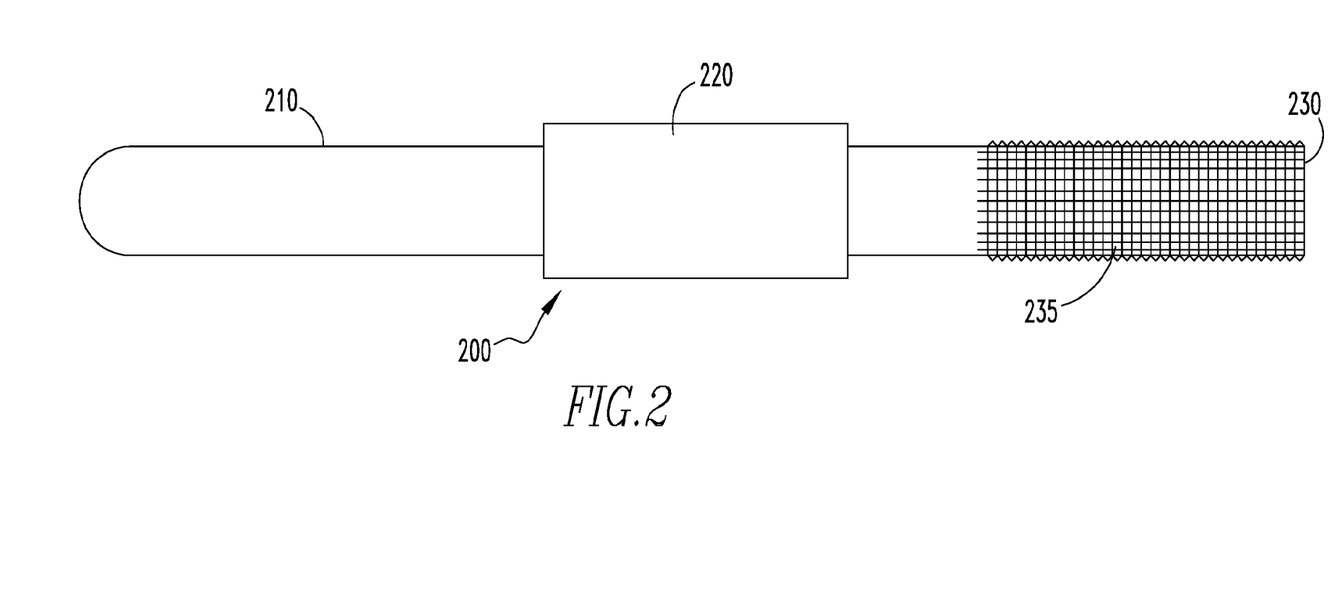
FIG. 2 is a perspective view of a combination clot forming tool.
Figure 3:
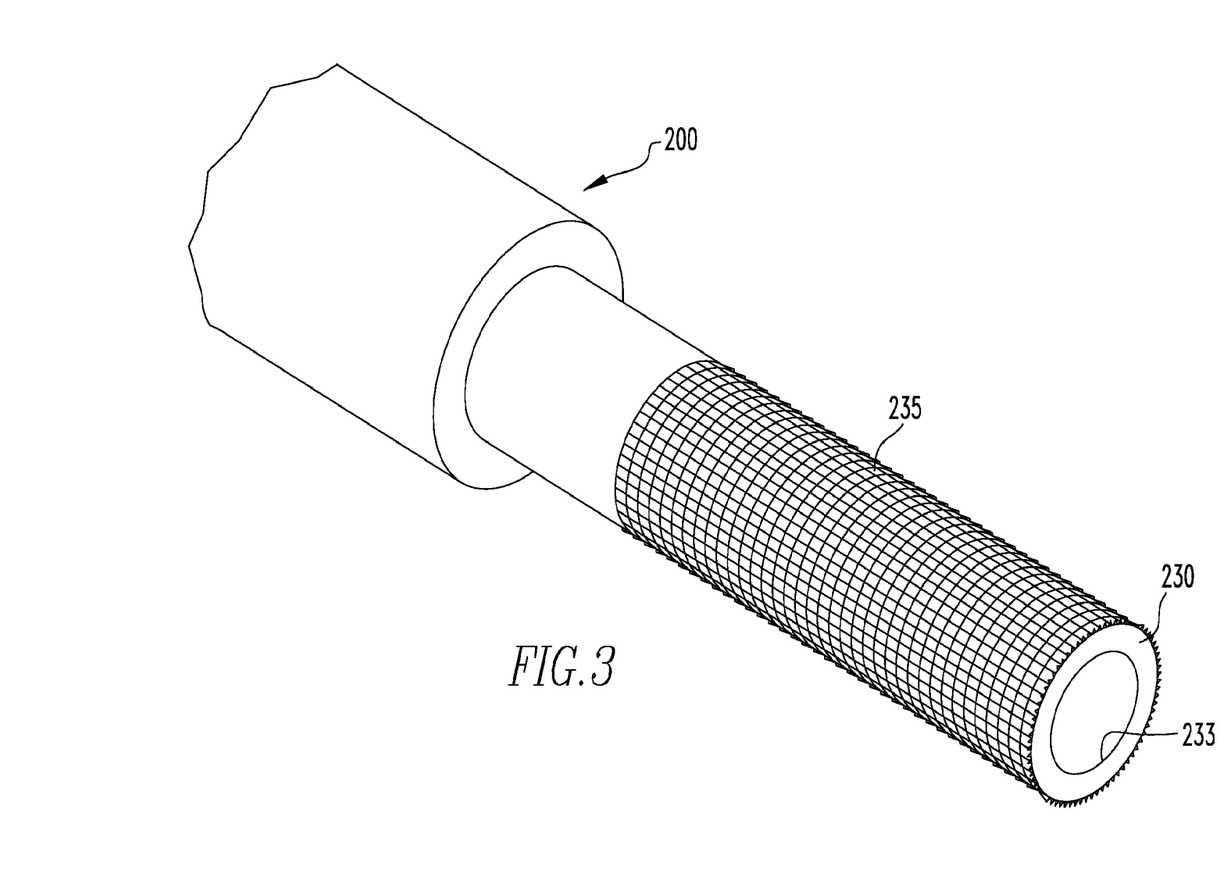
FIG. 3 is a perspective view of a distal end of the combination clot forming tool illustrated in FIG. 2.

An embodiment of the invention is a method of delivering graft material to a surgical site. The surgical site may be any surgical repair site that may benefit from the delivery of a graft material. For example and without limitation, the surgical site may be a meniscal repair site within a patient's knee such as a tear that is to be sutured or otherwise closed or amended. Acts of the method embodiment may include forming a clot 2000 (FIGS. 8 and 9) on a portion of a clot forming tool, such as the surface 235 of the clot collection end 230 of the combination clot forming tool 200, that has a first diameter. These acts in some embodiments include obtaining about a 60 CC volume of blood from a patient and placing the blood into a small beaker or other vessel (cup 600 in FIG. 7, for example). The blood is illustrated being stirred with a distal end of the combination clot forming tool 200 by the action arrow in FIG. 7. The distal end illustrated is the clot collection end 230 (FIGS. 2 and 3). The surface 235 depicted is a knurled surface, but in other embodiments may be etched surfaces, roughened surfaces, scored surfaces, coated surfaces, or any other surface capable of collecting clotting material, or portions with surfaces made from other materials upon which clots form, such as but not limited to glass, ceramic, and corrosion resistant metals such as stainless steel. More generally, a patient's or a donor's blood may be collected in the cup 600 and a tool or instrument may be used to stir or agitate the blood to promote clotting on a surface of the tool or instrument.

The method may include moving the clot 2000 from the clot forming tool 200 to a clot preparation device 100 that includes a base 110 and a work surface 120 supported on the base 110. The illustrated work surface 120 includes an upper working area 122, and a perimeter 130 around the upper working area 122 in at least part of which is formed a channel that is lower than an adjacent part of the upper working area 122 so that fluid placed on the upper working area 122 will drain into the channel under the force of gravity when the base 110 is placed on a horizontal surface. In the embodiment depicted, the work surface 120 includes multiple drainage openings 150 through the work surface 120. Moving of the clot 2000 that was deposited on the surface 235 from the clot forming tool 200 is specifically illustrated in FIG. 8. The clot 2000 being moved may include a single layer or in multiple layers of fibrin. In this illustration, the clot 2000 is being rolled off of the surface 235 and onto the gauze pad 1100 by rolling the clot forming tool 200 along the gauze pad 1100 (bottom of page to top of page as drawn). Other embodiments may not include an intermediary gauze pad 1100, and the clot 2000 may be placed directly on the work surface 120. In other embodiments, the moving of the clot 2000 may be accomplished using one or more other instruments that may be used to grasp the clot 2000 to remove the clot 2000 from the surface 235 and then place the clot 2000 onto the clot preparation device 100.

Method embodiments may also include pressing the clot 2000 against the upper working area 122 to remove liquid from the clot 2000 with a portion of the clot forming tool 200 that has a second diameter larger than the first diameter. In the illustration of FIG. 9, the roller 220 is the portion of the clot forming tool 200 being used to press the clot 2000 against the gauze pad 1100 and the upper working area 122 to remove liquid from the clot 2000. As used herein, the terms pressing the clot 2000 against the upper working area 122 includes pressing the clot 2000 against the gauze pad 1100 when the gauze pad 1100 is supported on the upper working area 122. The illustrated roller 220 is a middle region of the clot forming tool 200. The pressing illustrated in FIG. 9 is with a smooth surface configured to press against and flatten the clot 2000 without substantially adhering to the clot 2000.

Once the clot 2000 has been flattened, the clot 2000 must be prepared for delivery to the surgical site, typically by creating smaller pieces of the clot 2000. For example and without limitation, the clot 2000 may be held with forceps while scissors are used to cut the clot 2000 into thin strips or small pieces. The thin strips or small pieces may be placed directly into a surgical site, or an additional instrument may be used to deliver the thin strips or small pieces of the clot 2000 to the surgical site. One example delivery device 500 is shown in FIGS. 4-6. For the delivery device 500, delivering a portion of the clot 2000 to the surgical site may include placing strips or pieces into the delivery device 500 through the portal 504. The plunger 506 may be inserted through the portal 504 and advanced distally within the delivery device 500 to move strips or small pieces through the delivery device 500 and out of the distal end 501 of the delivery device 500. The proximal plunger 512 may be inserted through the proximal opening 515 and advanced distally within the delivery device 500 to move strips or small pieces through the delivery device 500 and out of the distal end 501 of the delivery device 500. The cap 511 at the distal end 501 is configured to be removed from the delivery device 500 before the delivery device 500 is in its final position for clot or graft delivery. As previously noted, several other delivery devices that could be used in various embodiments are disclosed in WO2018/169719A1, which has been incorporated by reference herein in its entirety.

In addition to loading a first clot delivery device, such as the delivery device 500, while the first clot delivery device is located in the first delivery device holder 105, after the first clot delivery device has been loaded, the first clot delivery device may be placed in a second delivery device holder 115 while a second clot delivery device is placed in the first delivery device holder 105 and loaded. In the illustrated example of FIGS. 5 and 6, the delivery device holder connector 155 of the first delivery device holder 105 couples with tubular body 510 of the delivery device 500 while the delivery device 500 is loaded. In addition to or as an alternative, delivering a portion of the pressed clot to the surgical site may include using an instrument for positioning a graft, such as the instrument for positioning a graft 3000 (FIG. 6), to place the pressed clot at the surgical site.

Various embodiments of an instrument or instrument set wholly or its components individually may be made from any biocompatible material. For example and without limitation, biocompatible materials may include in whole or in part: non-reinforced polymers, reinforced polymers, metals, ceramics, glass, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys.

Terms such as distal, proximal, below, horizontal, lower, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

The invention claimed is:

1. A clot preparation device comprising:
    a base having a topmost surface and a bottom surface configured to contact a horizontal surface, the topmost surface being sloped from a first edge of the base toward a second edge of the base with respect to the bottom surface;
    a work surface supported on the topmost surface of the base, the work surface comprising:
        an upper working area;
        a continuous channel extending around an outer periphery of the upper working area, at least a portion of the continuous channel extending lower than an adjacent part of the upper working area and an adjacent perimeter extending around an outer periphery of the continuous channel so that fluid placed on the upper working area will drain into the continuous channel under force of gravity when the bottom surface is placed on the horizontal surface; and
        at least one drainage opening defined through the work surface.

2. The clot preparation device of claim 1, wherein the work surface includes a lower working area below the upper working area configured such that fluid placed on the upper working area will drain into the lower working area under the force of gravity when the base is placed on the horizontal surface.

3. The clot preparation device of claim 2, wherein opposing sides of the base are sloped between the upper working area and the lower working area.

4. The clot preparation device of claim 2, further comprising a plurality of peaks at the upper working area configured to support a clot being prepared on the clot preparation device and a plurality of valleys at the lower working area.

5. The clot preparation device of claim 1, wherein the continuous channel includes the at least one drainage opening.

6. The clot preparation device of claim 1, further comprising a delivery device holder configured to receive a clot delivery device for delivering a portion of a clot graft to a surgical site, and wherein the delivery device holder comprises an indention in the clot preparation device.

7. The clot preparation device of claim 6, further comprising a supplemental delivery device holder configured to receive an additional delivery device.

8. The clot preparation device of claim 1, further comprising a delivery device holder connector into which a part of a clot delivery device for delivering a portion of a clot graft to a surgical site is releasably connectable.

9. The clot preparation device of claim 1, wherein the base is rectangular.

10. The clot preparation device of claim 1, wherein the continuous channel defined by the perimeter is spaced from the first and second edges of the base such that the perimeter extends between the first and second edges of the base and the outer periphery of the continuous channel.

11. The clot preparation device of claim 1, wherein the work surface is in a same plane as the topmost surface of the base.

12. The clot preparation device of claim 1, wherein the perimeter is in a same plane as the work surface.

\* \* \* \* \*